US005573727A

United States Patent [19]

Keefe

[11] Patent Number: 5,573,727
[45] Date of Patent: Nov. 12, 1996

[54] AUTOMATIC STAINING APPARATUS FOR SLIDE SPECIMENS

[75] Inventor: Raymond A. Keefe, Merbourne, Australia

[73] Assignee: Australian Biomedical Corporation Ltd., Australia

[21] Appl. No.: 331,662

[22] PCT Filed: May 13, 1993

[86] PCT No.: PCT/AU93/00219

§ 371 Date: Mar. 13, 1995

§ 102(e) Date: Mar. 13, 1995

[87] PCT Pub. No.: WO93/23732

PCT Pub. Date: Nov. 25, 1993

[30] Foreign Application Priority Data

May 13, 1992 [AU] Australia ................... PL2401

[51] Int. Cl.[6] ................................................ B05C 3/02
[52] U.S. Cl. ...................... 422/63; 436/48; 118/423
[58] Field of Search ........................ 422/63, 65, 102, 422/62; 436/46, 47, 48, 50, 43, 55; 118/425, 423, 419, 428

[56] References Cited

U.S. PATENT DOCUMENTS

| 3,604,436 | 9/1971 | Lipshaw | 134/76 |
|---|---|---|---|
| 3,691,988 | 9/1972 | Clarke | 118/6 |
| 3,837,795 | 9/1974 | Becker | 8/3 |
| 3,903,908 | 9/1975 | Logue | 134/57 R |
| 4,451,433 | 5/1984 | Yamashita | 422/63 |
| 4,738,824 | 4/1988 | Takeuchi | 422/63 |
| 4,911,098 | 3/1990 | Tabata | 118/423 |
| 5,104,621 | 4/1992 | Pfost | 422/67 |
| 5,209,903 | 5/1993 | Kanamori | 422/65 |
| 5,266,272 | 11/1993 | Griner | 422/104 |
| 5,282,149 | 1/1994 | Grandone | 364/497 |
| 5,324,479 | 5/1994 | Naldoni | 422/63 |

FOREIGN PATENT DOCUMENTS 63-208761  8/1988  Japan .

Primary Examiner—Jeffrey Snay
Assistant Examiner—Alexander Markoff
Attorney, Agent, or Firm—Cushman Darby & Cushman, L.L.P.

[57] ABSTRACT

An improved, automatic slide specimen staining apparatus. The apparatus includes a covered housing containing a plurality of baths, input and withdrawal drawers and a three direction slide racks transport mechanism. The transport mechanism is controlled in its movement of slide racks, from bath to bath between an initial position to a final position; the transport mechanism is under the control of a microprocessor control system programmed with a series of staining schedules that are operator selective for a given slide rack input from the initial position, the microprocessor control system interactively determining individual slide rack movement timing through selected baths.

15 Claims, 7 Drawing Sheets

AUTOMATIC STAINING APPARATUS FOR SLIDE SPECIMENS

This invention relates to an automatic staining apparatus for histochemical staining of tissue slide specimens and in particular to an improved automatic staining apparatus that can simultaneously process a plurality of slide specimens in accordance with different staining processes.

One known method of staining slide specimens is a "bicycle chain" apparatus wherein slide clips hold individual slides and the processing or staining of the slides according to a particular staining schedule occurs by the "bicycle chain" moving the slides across a linear collection of baths and the slides being immersed for a fixed period of 30 or 60 seconds in a particular bath and then being removed and moved to the next scheduled bath.

This apparatus however is labour intensive when coping with a multitude of slide specimens as each slide clip only holds a single slide. In a normal day at a large laboratory it may be necessary to process some 3,000 slides, therefore this process is highly inadequate. Further the "bicycle chain" apparatus is not economical in its processing as it has fixed immersion times, therefore if a schedule requires a shorter or longer immersion time, the chemical effect must be achieved by altering the concentrations of the chemicals. This requires either continual alteration of the concentration of chemicals in a particular bath or a plurality of baths with the same chemicals but at different concentrations. A large number of baths is therefore needed to provide a variety of schedules. The "bicycle chain" apparatus is also uneconomical in that in a linear system the time of travel from one bath at one end of the apparatus to the scheduled next bath, for a slide to be immersed in, at the other end of the apparatus, may substantially lengthen the time within which the staining procedure of a plurality of slides is completed.

Another known apparatus for automatic staining of slide specimens is a batch stainer apparatus wherein a basket holds a plurality of slides and the apparatus processes the slides according to a single staining procedure or schedule. However the next batch of slide specimens is not able to be processed until the first batch has completed its schedule and been removed from the apparatus. As a staining schedule may take from ½ to 3 hours then either a plurality of machines is needed or the length of time for processing the plurality of slide specimens is substantially lengthened. It is usually also uneconomical to proceed until the basket holding the slides is completely full.

It is therefore an object of this invention to provide an improved automatic staining apparatus which overcomes one or more of the aforementioned disadvantages of known machines.

According to one aspect of the invention there is provided automatic tissue staining apparatus for staining tissue slide specimens, said apparatus comprising one or more slide racks each adapted to contain a plurality of said slides, a plurality of baths for containing chemicals for treating said specimens, said baths being located within a casing, and means for moving a said rack from one said bath to another, according to a microprocessor controlled programmable staining schedule, characterised in that, said microprocessor is programmable with different staining schedules and contains logic whereby multiple schedules can operate simultaneously.

In order that the invention is more readily understood a particular embodiment thereof will now be described by way of example only with reference to the accompanying drawings wherein.

Figure 1:
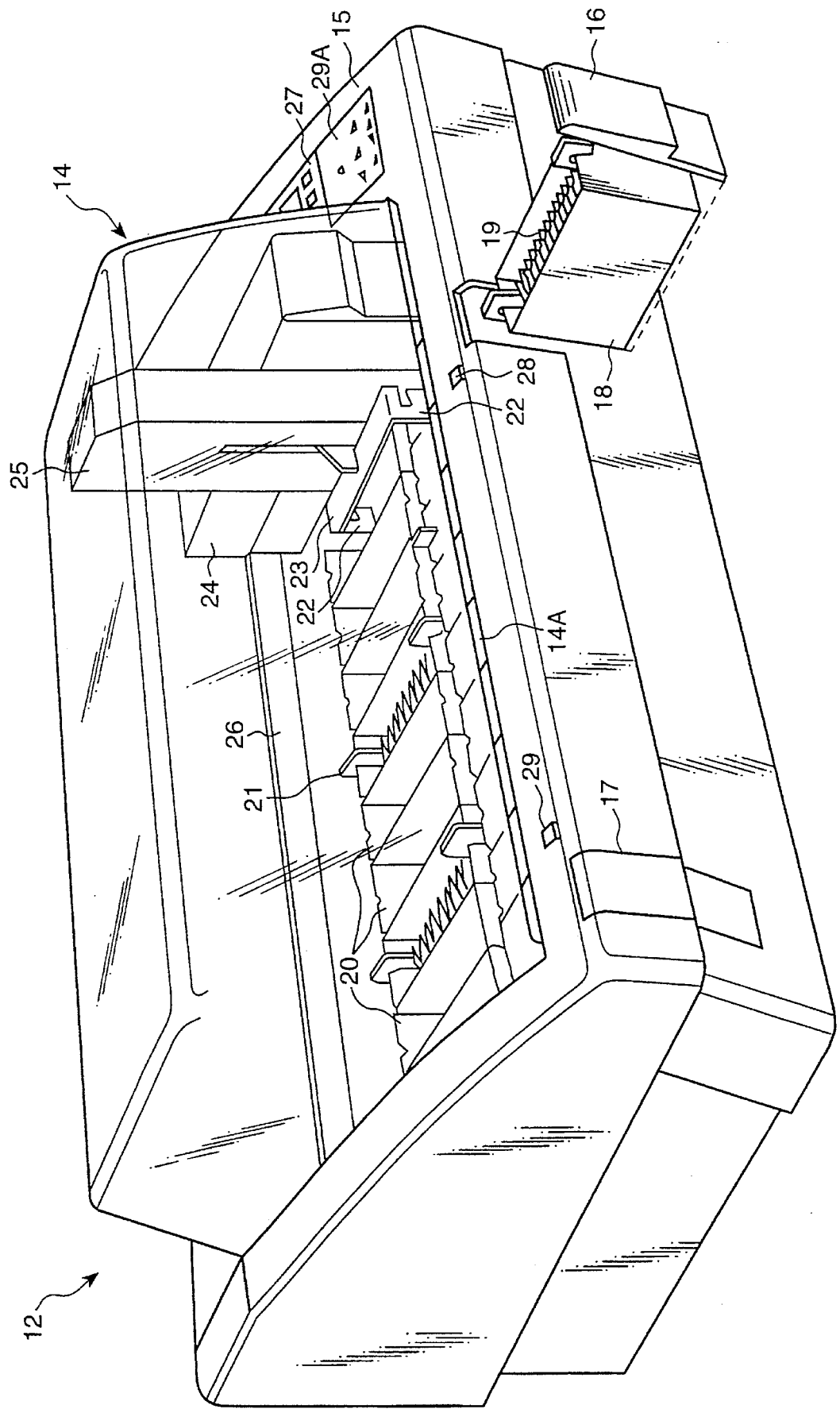
FIG. 1 is a perspective view from above of an automatic staining apparatus in accordance with the invention.

Referring to the drawings, an automatic staining apparatus comprises a casing 12 forming an enclosure. Said casing comprises a body 15 and a fume cover 14. The casing 12 further includes a toxic fume filter (not shown) which is able to absorb the toxic fumes normally associated with staining processes such as for example xylene. One particular example of a filter which can absorb xylene is an activated charcoal filter. Between the fume cover 14 and the body 15 of the casing there is a gap 14a. A fan (not shown) draws external air into the casing 12 through this gap 14a and expels fumes generated from the baths through an exhaust vent (not shown) after these fumes have been treated by the toxic fume filter.

Within the casing 12 are a plurality of baths 20 for holding various concentrations of chemicals needed for the staining treatment of slide specimens. These baths are arranged an array comprising two parallel rows. This array may be linear, but is preferably a two-dimensional array as shown in order to reduce the distances between any two baths. Slide racks 21 are configured to fit into the baths, one at a time, and to allow immersion of the relevant portions of the slide specimens in order that staining can occur.

To further ensure containment of toxic fumes and to minimize the escape of fumes when loading or unloading a rack of slides 21 into the casing drawers 16 and 17 are provided for inputting and outputting the slide racks, respectively. A rack 19 to be inputted is placed into an input bath 18 supported on drawer 16 which is then slid back into the casing. The input bath 18 is then aligned with the other baths of a row within the casing. After processing, the drawer 17 is similarly used to withdraw the completed rack from the enclosure means. Although the fume cover 14 is able to be opened in order to access the baths and racks and to do general maintenance the use of the drawers 16 and 17 minimizes the escape of fumes from the enclosure means whether the drawers are-open or closed thereby enhancing the safe working conditions of the operator.

A carriage arrangement is located within said casing above the array of baths and consists of a linear guide rail 26 in the form of a rod extending along the back of the casing and a carriage 24 supported by said rail and adapted for movement along the guide rail. The rod in fact passes through a bearing (not shown) in the carriage whereby the carriage is pivotal on the rod. The carriage 24 includes a hoist 25 which is adapted to move transversely across the carriage 24, that is, in a direction towards and away from said guide rail. The hoist 25 includes a cross-member 23 which is arranged to be moved vertically on the hoist 25. The carriage arrangement therefore provides XYZ movement of the cross-member 23 whereby the cross-member is able to move in three mutually perpendicular directions separately or simultaneously. The carriage 24 is able to move the hoist 25 anywhere in a plane parallel to the plane of the collective tops of the baths 20. This is achieved by moving the carriage 24 along the linear guide rail 26 and by the hoist 25 moving along the length of the carriage 24. The carriage 24 has ball bearing rollers (not shown) at the front end which bear on a flat metal strip (not shown) extending along the inside front of the casing so as to support the carriage arrangement. To obtain the third direction of travel, the hoist 25 is able to move the cross-member 23 in a vertical direction thereby resulting in XYZ movement of the cross-member 23. This means the cross-member 23 has maximum flexibility and is able to proceed to any other position from any position at any time and due to the array system of the baths the time for processing staining schedules of a plurality of slides in a plurality of slide racks has been dramatically decreased. The cross-member 23 has respective hook members 22 for engaging a slide rack as will be described hereinbelow.

Each directional movement of the components of the carriage arrangement is effected by a separate stepper motor (not shown) which drives a separate cable (also not shown) extending along each axis.

The staining apparatus further includes a keypad 27 located on the body 15 and switch 28 located near the input drawer 16. A microprocessor is also contained within the body 15.

In operation the baths are filled with particular concentrations of staining chemicals or washing chemicals used between staining steps and then placed in the array which would have been predefined into the microprocessor. A first position in the array is the position into which input bath 18 slides when the drawer 16 is closed. A last position of the array is the position in which the bath is located when it is in drawer 17 and the drawer 17 is closed. The operator can then define a staining schedule into the microprocessor through the keypad 27, the schedule would usually begin at the first position and finish at the last position. However further flexibility is allowed since the fume cover is able to open and thereby any position can be defined in the schedule as the finishing position. If one or more schedules are already in the microprocessor then the keypad 27 can be used to indicate which of the memorized schedules is to be used for the further slide rack 19 being inputted at the first position.

Once the schedule of the chemical baths 20 has been inputted into the microprocessor by way of the keypad 27, the rack 19 is inputted into the input bath 18 connected to the drawer 16 and the drawer is closed to then place the further rack 19 into the first position of the fixed array within the casing 12. The operator then selects the required programmed schedule stored in the microprocessor by means of the keypad 27 or alternatively programs in a further schedule and presses an input button 28 to indicate that the further slide rack is now in the first position. The input button 28 may be replaced by a sensor that detects the presence of a further slide rack in the first position, however better control is believed to be obtained by use of a stop start system whereby the input switch 28 acts as a start system for the microprocessor to control the movement of the slide rack 19. If the slide rack 19 is the first and only slide rack that is undergoing a specified staining schedule, then the control means will direct the movement of the carriage arrangement 22 so that the cross-member 23 lifts the slide rack out of the input bath and into the subsequent baths according to the selected programmed schedule. For this purpose the cross-member 23 is provided with end hooks 22 which engage with respective lifting arms 47 of the slide rack 19 as will be described in more detail hereinbelow.

As well as moving the slide racks between baths, the cross-member 23 is also able to impart an agitation to the slide rack in order to enhance either the staining procedure or a washing procedure and is effected by a movement of the cross-member 23. After completing the scheduled staining procedure through the required baths the final step would usually be movement to the last position of the array located where a bath is located in the drawer 17. Indicator light 29 shows when a slide rack has arrived at the last position and is ready for removal through the exit drawer 17. The indicator light may be initiated by a sensor detecting the presence of a slide rack in the drawer position 17 or it may receive an indication from the control means, that is, the microprocessor that the selected programmed schedule for this particular rack has been completed and the rack is now in the last position. If the rack is not removed within a specified time the microprocessor 19 might also emit an audible alarm to advise the operator to withdraw the completed slide rack. When the apparatus has completed a schedule that ends with the slide rack in any other station except in the output drawer 17, then an unload indicator light 29A will be turned on and an audible alarm signal will sound. The user will be required to suspend the operation of the other slide racks whilst opening the fume cover 14 and removing the slide rack and this may be done automatically by a sensor (not shown) which detects opening of the cover. After closing the fume cover 14 normal operation is automatically restarted or an operation of the keypad is used to firstly suspend operation and then to restart operation of the staining apparatus.

The staining apparatus however, is particularly beneficial for processing a plurality of slide racks simultaneously. Usually the slide racks would be entered one at a time through the entrance drawer 16 into the first position of the array within the casing 12. Upon the operator closing the drawer 16, selecting the required schedule or programming a further schedule via the keypad 27, and by initiating control of the further slide rack by pressing switch 28, the microprocessor then makes a series of assessments before starting the movement of the rack through the selected schedule. In a simple schedule a slide rack may proceed through a series of baths and never be immersed in the same bath twice. In this simple case any following slide racks merely need to be delayed for a certain time in order to avoid any clashes caused by the further slide rack "catching up" with the previous slide rack. The microprocessor is able to assess the time delay required to avoid these clashes and thereby delays the starting of the staining schedule of the further slide rack until this time delay has elapsed. Although the carriage arrangement and its XYZ capability for movement has dramatically decreased the travel time between subsequent baths, the control system microprocessor must also take into consideration an element of travel time in moving between various racks and also since in this particular embodiment there is only one movement means, no two scheduled steps can occur at the same time. The control means microprocessor means must therefore not only allow for the delay time needed to avoid clashes but also the travel time of the carriage arrangement and the meshing of the schedules in order that the movement arm only needs to move one slide rack from one bath to the next at any one point in time.

Even when using a simple schedule the control of a plurality of slide racks can be complicated. However the automatic staining apparatus of the present invention is able to cope with a plurality of slide racks and a plurality of schedules with different slide racks following different schedules in order to achieve this, the microprocessor makes a further assessment which is based on the delay times allowed in any particular scheduled step. These delay times or variations in steps of a schedule may be inputted before a schedule begins or would usually be included into the memory when the schedule is first programmed. These variations of times would be due to the steps required in staining procedures including immersion in staining chemicals as well as in washing chemicals. The time that a plurality of slide specimens in a slide rack is able to remain in a washing chemical bath is usually less critical than the time allowed for the slide rack to remain in a chemical staining bath. Thereby-once the initial schedule has been inputted into the microprocessor and the variation times have been inputted into the microprocessor, the operator merely needs to place the further slide rack 19 into the input drawer 16, select the required program via the keypad 27, close the drawer 16 and initiate the control means (microprocessor) to control the further slide rack 19 by pressing the switch 28. The microprocessor then assesses when and to what schedule the further slide rack 19 will proceed. This assessment includes amendment of the selected schedule of the further rack 19 in accordance with the allowable variations as well as amendment of the selected programs of the slide racks that have already began to be processed according to the allowable variations in their schedules so as to provide optimum scheduling. Upon the microprocessor determining the best meshed schedules of the further slide rack as well as the slide racks already being processed, the microprocessor controls the movement of the carriage arrangement in order for the further slide rack 19 to proceed according to the assessed schedule. The schedule may also include a delay time at the beginning.

In the preferred form of assessment of the scheduling, the following steps occur in the microprocessor. For each rack, and for each step, at the time specified in the program, the time is calculated to get the rack from where it is and move it onto the next bath, agitate it and release it. Where processing of racks has already begun, the steps already completed are removed and the times offset to reflect the actual state of progress of the racks. A loop is now entered in the microprocessor program that attempts to complete the assessment of the staining of all racks by assigning times at which racks are to be moved from station to station, that is, from bath to bath. The loop proceeds as follows. For each rack get the next group of events up to an immersion that is allowed to be extended; sort these into the order of earliest to latest non-extensible, that is critical, immersions followed by earliest to latest extensible, that is non-critical incubations. If two events are at the same time and of the same priority then the rack which was inserted earlier gets precedence; using the above ordering attempt to find a time offset (0 to infinity) which permits all events in a group to be done without clashing in time or station use with any other event. If the current immersion is non-extensible then the offset must be zero. If a suitable offset is found then this group of events is placed in the processing schedule otherwise it is put aside until the next round. The above process is done for each group of events for each rack in the order defined until no more events can be scheduled. The above loop is repeated until no more events can be scheduled. Once all events that can be handled have been scheduled into one meshed schedule, these events are then processed.

Figure 4:
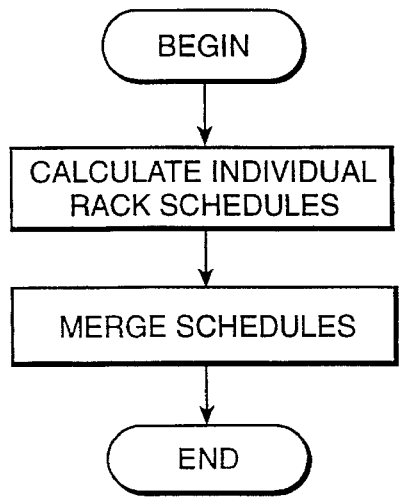
FIG. 4 is a flowchart of the overall process in accordance with the invention.
Figure 5:
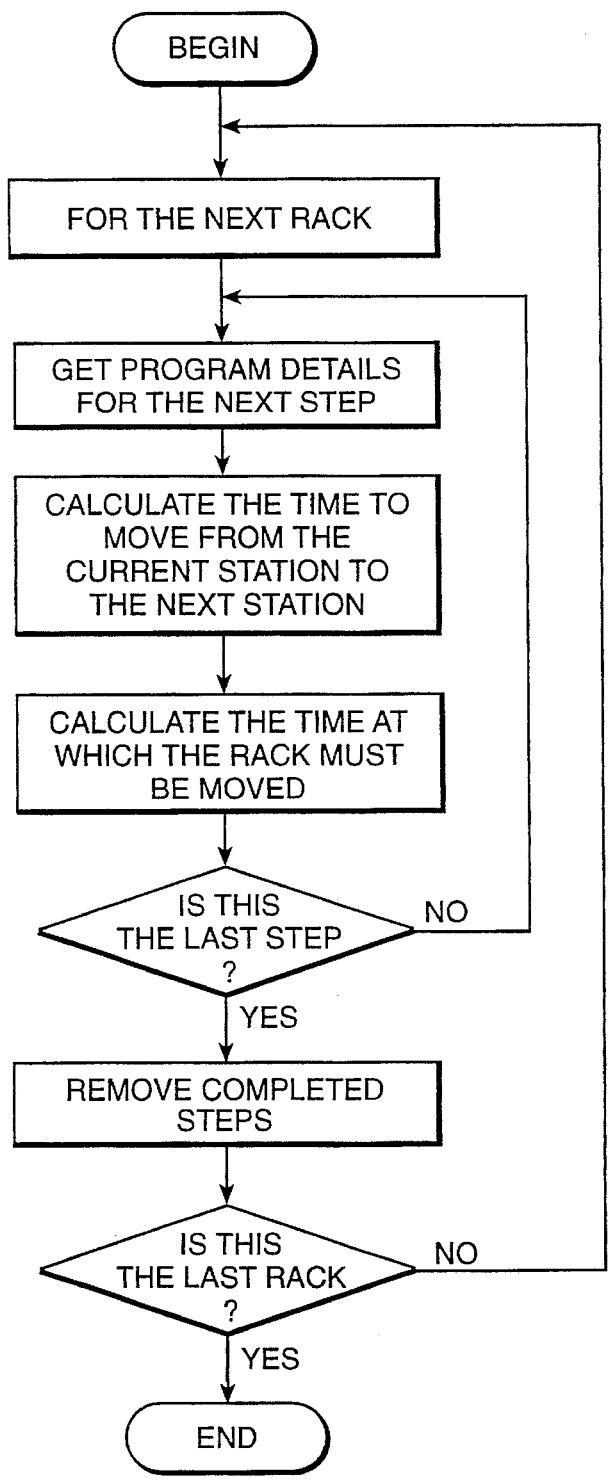
FIG. 5 is a flowchart of the first part of the process of the invention as shown in FIG. 4 which calculate individual rack schedules.
Figure 6A:
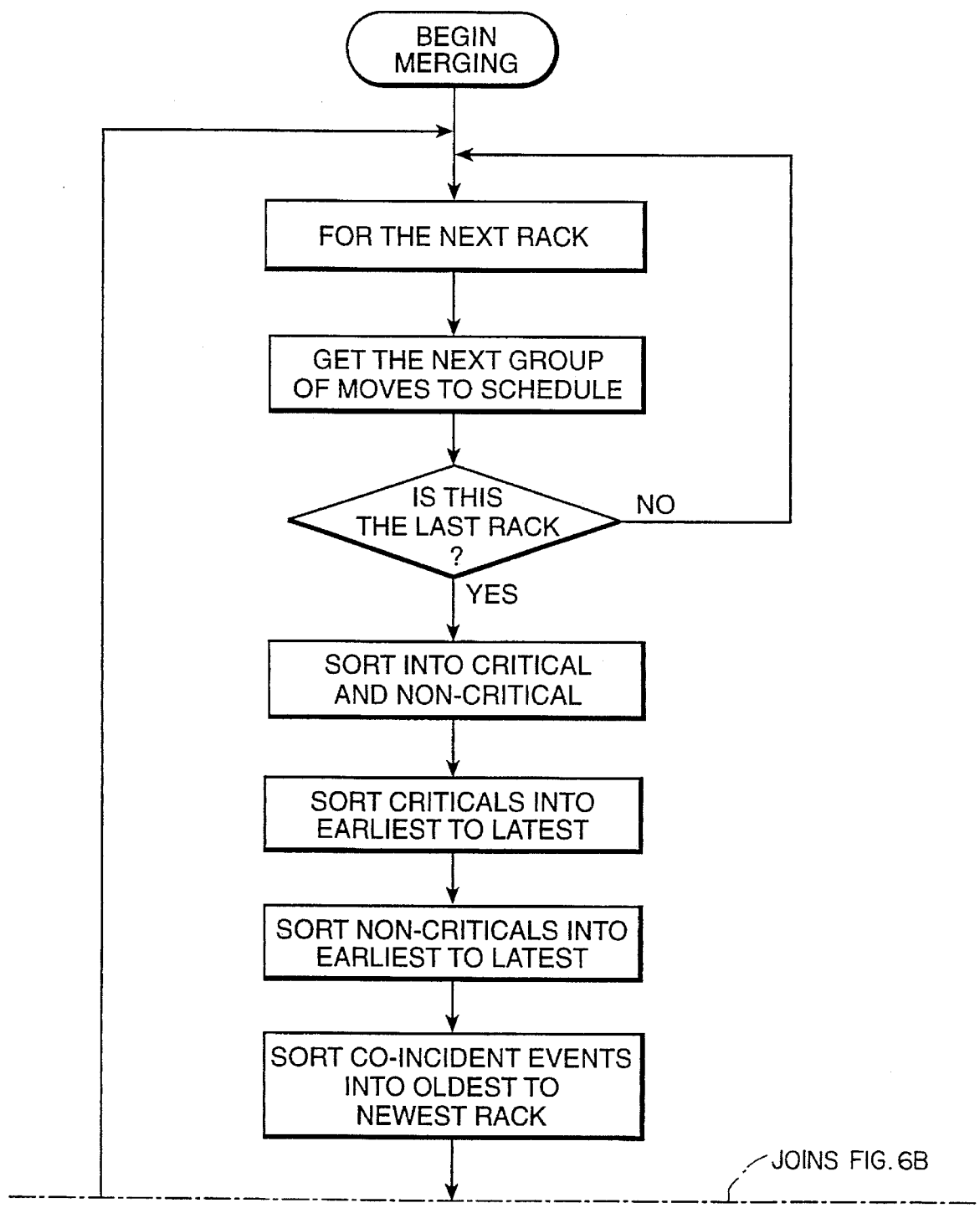
FIGS. 6A, 6B, 6C are a flowchart of the second part of the process of the invention as shown in FIG. 4 which merge schedules.
Figure 6B:
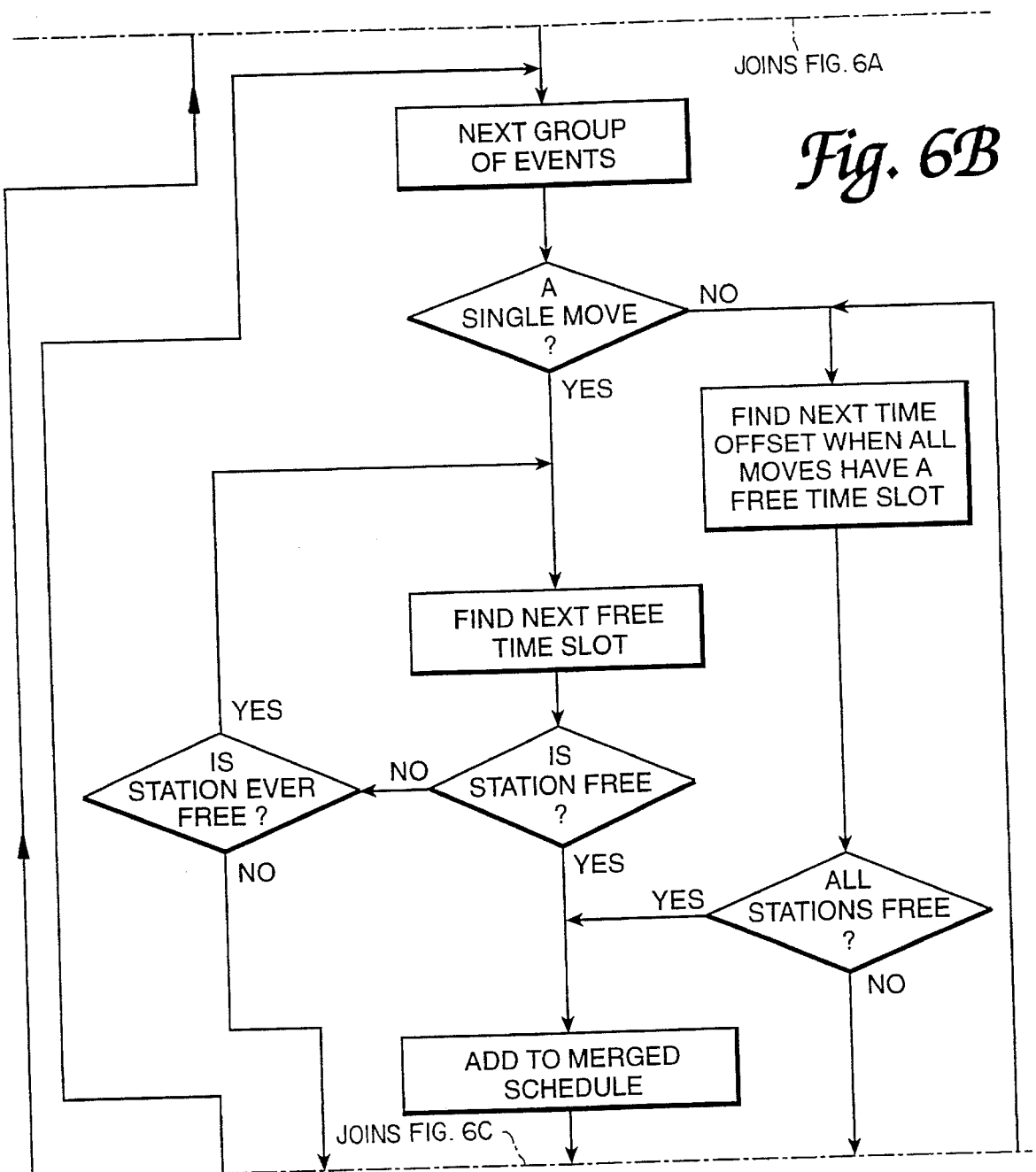
Figure 6C:
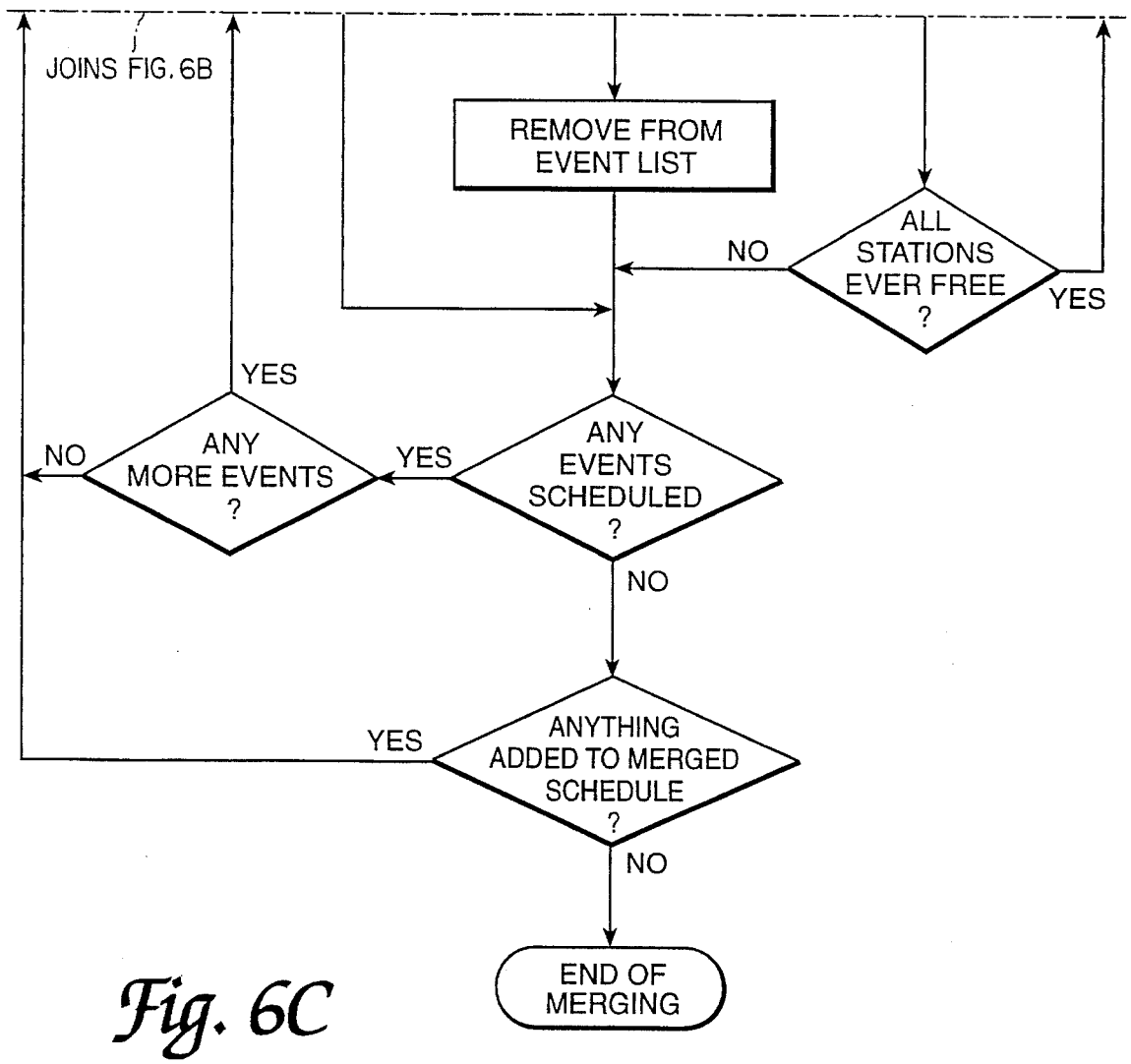

FIG. 4 shows the main flow chart for the process described above including the calculation of individual rack schedules followed by the merging of schedules. FIGS. 5 and 6A–6C show the detailed steps in the calculation of individual rack schedules and merging of schedules respectively.

Whenever a new rack is added or an existing rack is completed and/or removed from the apparatus, a new schedule is compiled. Thus, the control system includes means for establishing a staining schedule for each slide rack and for reestablishing the staining schedule when a slide rack is inserted into or removed from said apparatus. This scheduling technique makes sure that two racks are not required to be moved at the same time and that two racks never attempt to occupy the same bath at the same time. It allows multiple racks of slides to be stained simultaneously with different programs and for new racks to be added at any time without disturbing existing racks.

As there is a plurality of slide racks being processed at the same time and in order for an operator not to have to be present at all times to remove the slide rack in drawer 17, there may be a plurality of finishing drawers located near exit drawer 17 which are the final steps of the schedule. The microprocessor may therefore amend the schedule of following slide racks so that if the indicator light 29 is still on, the microprocessor will then direct the carriage arrangement to leave the further slide racks in other nominated final baths.

For certain combinations of programs, especially when there is a lot of back-tracking of slide racks into a particular bath for a plurality of times, there may be no better solution for the further rack to be processed rather than wait until the previous racks have completed their schedules. Usually however, the contents of the baths could be duplicated in order to minimize this occurrence but it would be expected that a particular laboratory would usually run a preferred number of schedules and these could be optimized by the selection of baths and the minimization of use of a bath for a plurality of times. Further in order to stop the microprocessor going off on an everlasting calculation of the best meshed schedule, there is a series of criteria to be first met and if certain criteria are met then the assessment of the selected schedule of the further slide rack 19 can be cancelled. The operator is then either notified by an audible or visual signal or the schedule is automatically delayed until the processing of the slide racks already undergoing staining procedures has been completed or until a predetermined time has elapsed. The series of criteria is then rechecked and if the criteria are no longer attained then the assessment means proceeds to assess the best meshed schedule including the selected schedule of the further slide rack.

Figure 2:
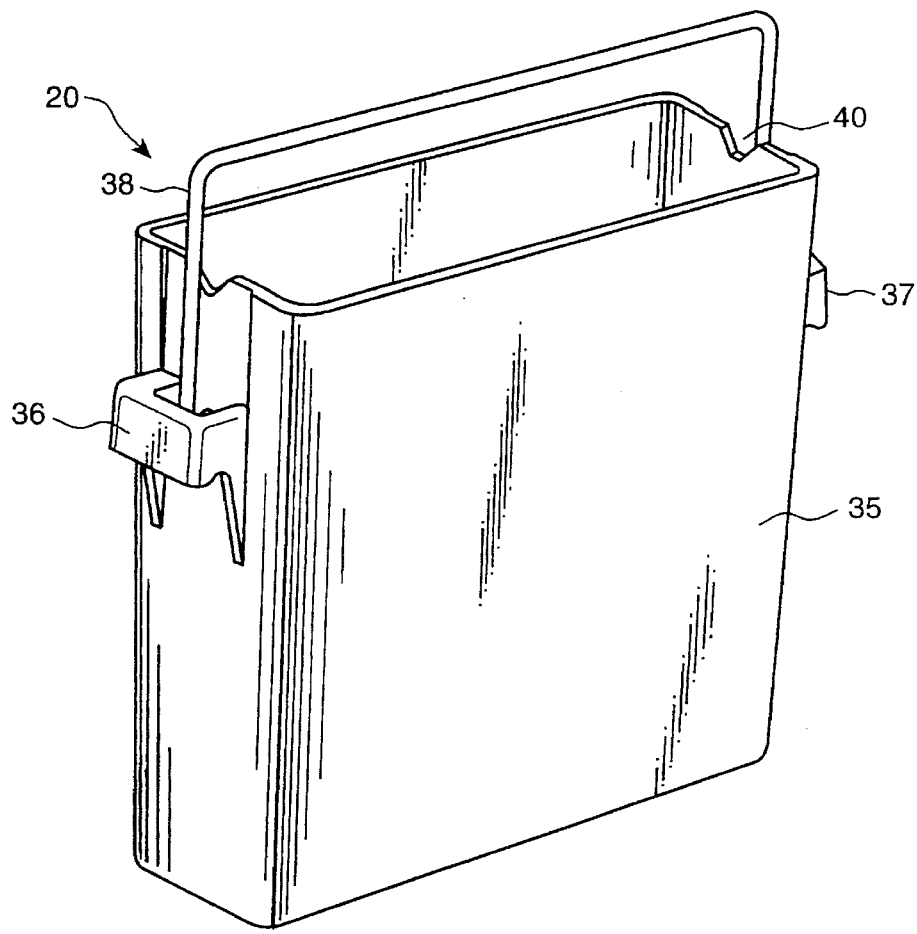
FIG. 2 is a perspective view from above of a bath in accordance with the invention.
Figure 2A:
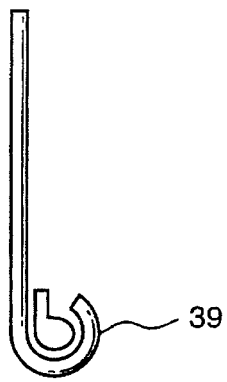
FIG. 2a is a side view of the handle of the bath of FIG. 2.

FIG. 2 shows a particularly preferred embodiment of a chemical or reagent bath 20 comprising a body 35 in the form of a container for the reagent or washing chemical, side brackets 36 and 37 on opposite sides of the body, respectively, and handle 38 which extends from the side brackets in order to make it easily removable from the array within the casing. The handle 38 is constructed, as shown in FIG. 2(a), to include end portions 39 which sit in the side brackets 36 and 37, respectively. The centre of gravity of the handle is such as to ensure that the handle does not remain in an upright position, but automatically falls to the side when not being held aloft. This ensures that in operation of the staining apparatus, the carriage arrangement does not become entangled in the handle and is able to access the slide racks contained within the array of baths 20.

Figure 3:
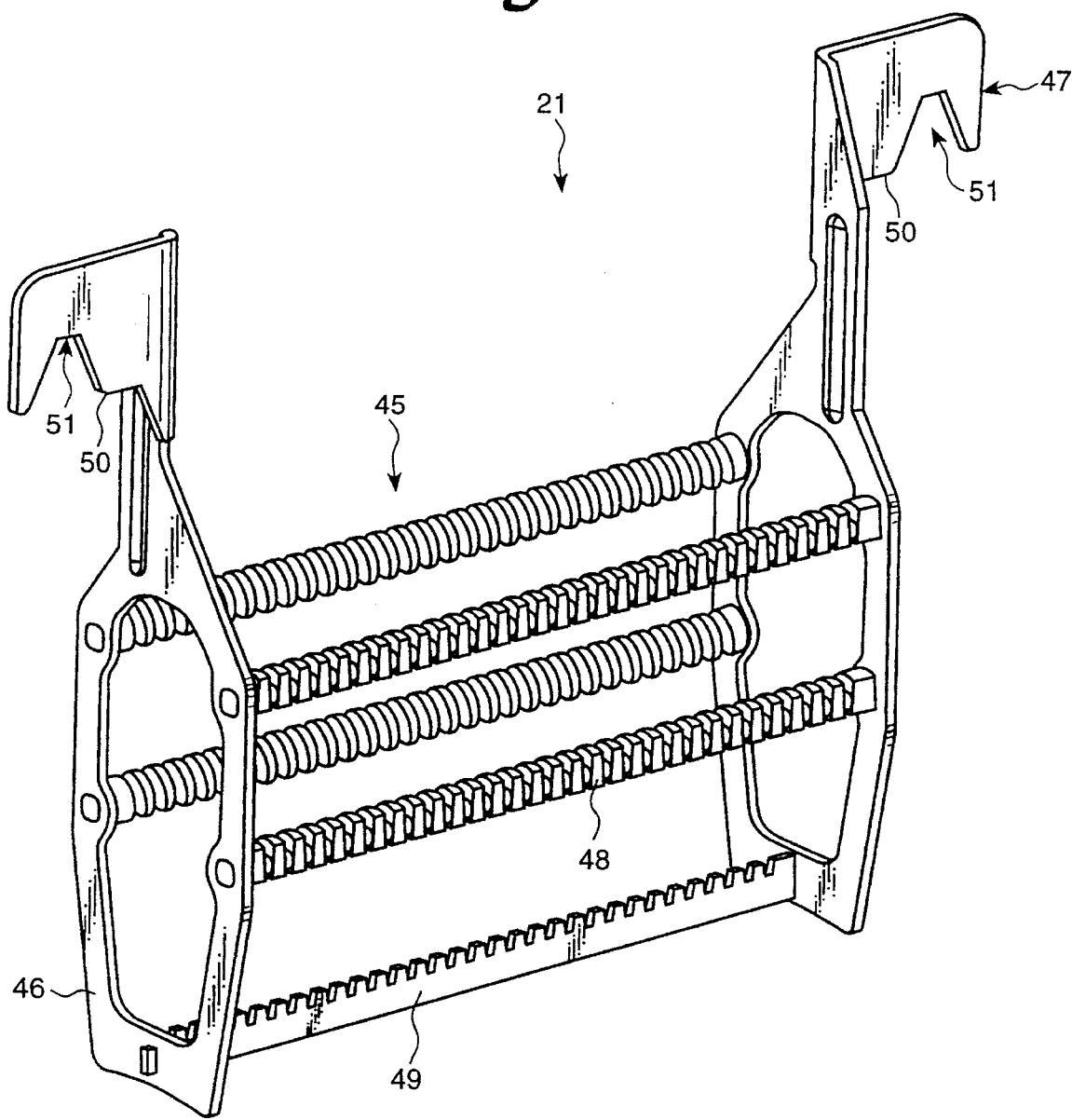
FIG. 3 is a perspective view of a slide rack in accordance with the invention.

Referring to FIG. 3, a perspective view of a slide rack is shown. The slide rack consists of end panels 46 each extending up to a respective holding arm 47. Between the two end panels 46 four identical support bars 45, and a base support member 49, extend in a spaced parallel relationship. The support bars 45 each comprise a series of quarter circle segments 48 arranged on respective rods which extend between the end panels. The segments 48 have tapered sides such that they define a groove therebetween which accommodates an edge of a slide (not shown) containing a specimen to be processed. The spacing of the support bars 45 is such that a generally rectangular slide may be slid downwardly between the bars 45 whereby opposite edges of the slide are held between corresponding grooves of the top two and the bottom two bars. The base support member 49 has notches which support a bottom edge of the slide midway between the opposite edges. The shape of the support bars 45 and the base support member 49 has been established empirically so as to provide maximum drainage of chemical reagent or washing chemical when a rack is withdrawn from a bath 20. In other words the design of the slide rack is such as to provide minimum surface tension between the rack and the chemical in the baths 20 whereby the chemical drains to a maximum degree from the rack as it is withdrawn from the bath.

In operation therefore a plurality of slides are held vertically within the slide rack by being positioned between the four bars 45 and the base member 49. By holding the slides in fixed vertical positions, then constant processing or staining of the slides is maintained since no two slides will be touching each other and the possible vertical gradient of the chemicals in bath will similarly effect all of the slides. To further ensure constant and effective staining, the bars 45 are minimized in size and have hydrodynamic sections to maximize fluid run-off. Similarly the supporting bar is a thin vertical bar to allow the liquid to easily infiltrate between the slides and not cause an overflow of the liquid in the bath as would result if there is a broad supporting bar. In operation the holding arms 47 extend over the recesses 40 (FIG. 2) of the chemical baths 20 and a horizontal ledge 50 of the holding arm rests on the base of the respective recess 40. The holding arms 47 have an inverted groove 51 which is engaged by a hook 22 of the cross-member 23 of the carriage so that the slide rack may be lifted from or placed into the chemical baths 20. Naturally the chemical baths 20 are dimensioned to hold a slide rack so that the slides within the slide rack are immersed in the liquid being held by the chemical baths 20.

It should be evident from the description hereinabove that the present invention provides an improved automatic staining apparatus and method for staining a plurality of slide specimens held in a plurality of slide racks which avoids most, if not all, of the disadvantages of the prior art. Of course many modifications to the above described embodiment may be readily envisaged by persons skilled in the art. For example, there may be a plurality of carriage arrangements and/or a plurality of drawers to input and output slides or, alternatively there may only be one drawer which does both operations.

I claim:

1. Automatic tissue staining apparatus for staining tissue slide specimens, said apparatus comprising a housing including a closeable cover assembly, a plurality of slide racks each containing a plurality of individual slides containing specimens, a plurality of baths each containing chemicals for treating said specimens, means for moving a said slide rack from one of said plurality of baths to another of said plurality of baths, and a control system including a programmable microprocessor, said control system including means for inputting a schedule of said baths, thereby defining a programmed staining schedule and for selecting a programmed staining schedule for a slide rack inserted into said apparatus, said control system providing selectable control over said moving means to control slide rack movement through a programmed sequence through said plurality of baths, defined by said staining schedule, said microprocessor being programmable to iteratively determine movement timing of each slide rack within said plurality of slide racks whereby multiple schedules of movement of various ones of said plurality of slide racks can operate simultaneously, means for inputting additional slide racks and means for withdrawing processed slide racks, said control system further including means for indicating the insertion of additional slide racks into said apparatus and the withdrawal of slide racks from said apparatus, said control system including means for establishing a staining schedule for each slide rack and for reestablishing the staining schedule when a slide rack is inserted into or removed from said apparatus.

2. Automatic tissue staining apparatus as defined in claim 1, wherein said slide rack inputting means includes a first drawer assembly movable between a first closed position and a second open position for accommodating a slide rack to be introduced into said apparatus whereby when said first drawer assembly is in the closed position a slide rack therein may be lifted therefrom or placed therein by said means for moving said one or more slide racks from one of said plurality of baths to another.

3. Automatic tissue staining apparatus as defined in claim 2, wherein said slide rack withdrawing means includes at least one second drawer assembly, movable between a first closed position and a second open position wherein at least one slide rack which has completed a schedule is placed by said means for moving each slide rack from one said bath to another into said at least one second drawer assembly to thereby permit removal of the slide rack placed therein from said apparatus by opening said second drawer assembly.

4. Automatic tissue staining apparatus as defined in claim 2, wherein said control system controls immersion times for each one of said slide racks in selected ones of said plurality of baths.

5. Automatic tissue staining apparatus as defined in claim 2, further comprising means for generating a signal and communicating said signal to said microprocessor when said first drawer assembly is moved to its closed position whereby said microprocessor is initialized to commence operation of said reestablished staining schedule.

6. Automatic tissue staining apparatus as defined in claim 3, further comprising means for generating a signal when a slide rack is in said second drawer assembly and ready for removal from said apparatus.

7. Automatic tissue staining apparatus as in claim 3 wherein the control system means for reestablishing of said staining schedule for said plurality of slide racks includes means for delaying commencement of a staining schedule for an inserted slide rack until commencement thereof interfits with the staining schedule for the remaining ones of said plurality of slide racks.

8. Automatic tissue staining apparatus as defined in claim 1, wherein said control system controls immersion times for each one of said slide racks in selected ones of said plurality of baths.

9. Automatic tissue staining apparatus as defined in claim 1, wherein said control system is selectively programmable to receive additional staining schedules for additional slide racks without disruption to slide rack, staining schedules currently operating.

10. Automatic tissue staining apparatus, as defined in claim 9, wherein said means for moving comprises a carriage arrangement including engagement means for releasably engaging one of said plurality of slide racks for the purpose of lifting, transporting and releasing the engaged slide rack.

11. Automatic tissue staining apparatus as defined in claim 10, wherein said carriage arrangement is movable along XYZ axes.

12. Automatic tissue staining apparatus as defined in claim 11, wherein each of said plurality of baths includes a handle pivotally attached thereto, said handle being pivoted to a vertical position for manually lifting a bath, said handle being pivoted downwardly so as to be positioned along a side of each of said plurality of baths when a bath not being lifted.

13. Automatic tissue staining apparatus as in claim 1 wherein the control system means for reestablishing of said staining schedule for said plurality of slide racks includes means for delaying commencement of a staining schedule for an inserted slide rack until commencement thereof interfits with the staining schedule for the remaining ones of said plurality of slide racks.

14. Automatic tissue staining apparatus as in claim 1 wherein said means for indicating includes a manually operable signal generator.

15. Automatic tissue staining apparatus as in claim 14 wherein said manually operable signal generator comprises a keypad.

* * * * *